(12) United States Patent
Koppe et al.

(10) Patent No.: US 8,951,584 B2
(45) Date of Patent: Feb. 10, 2015

(54) FEED FOR FISH

(75) Inventors: Wolfgang Koppe, Stavanger (NO); Alex Obach, Stavanger (NO); Ramon Fontanillas, Barcelona (ES)

(73) Assignee: Trouw International B.V., Boxmeer (NL)

( * ) Notice: Subject to any disclaimer, the term of this patent is extended or adjusted under 35 U.S.C. 154(b) by 90 days.

(21) Appl. No.: 12/278,536

(22) PCT Filed: Jan. 16, 2007

(86) PCT No.: PCT/EP2007/050393
§ 371 (c)(1),
(2), (4) Date: Oct. 28, 2008

(87) PCT Pub. No.: WO2007/090714
PCT Pub. Date: Aug. 16, 2007

(65) Prior Publication Data
US 2009/0162455 A1   Jun. 25, 2009

(30) Foreign Application Priority Data

Feb. 7, 2006   (GB) .................................. 0602426.9

(51) Int. Cl.
*A61K 36/537* (2006.01)
*A61K 36/00* (2006.01)
*A23L 1/00* (2006.01)

(52) U.S. Cl.
USPC ........... 424/746; 426/273; 426/276; 426/285; 426/289; 426/293; 426/302; 426/89; 426/98; 426/615; 426/648; 426/651; 426/655; 424/725

(58) Field of Classification Search
USPC .......... 424/746, 725; 426/273, 276, 285, 289, 426/293, 302, 89, 98, 615, 648, 651, 655, 2
See application file for complete search history.

(56) References Cited

U.S. PATENT DOCUMENTS

| | | | | |
|---|---|---|---|---|
| 2004/0131709 | A1* | 7/2004 | Berdahl et al. ................. | 424/745 |
| 2006/0286184 | A1* | 12/2006 | Nativ et al. .................... | 424/746 |
| 2007/0281044 | A1* | 12/2007 | Mueller et al. ................. | 424/727 |

FOREIGN PATENT DOCUMENTS

| | | |
|---|---|---|
| EP | 1 208 751 | 5/2002 |
| EP | 1 314 358 | 5/2003 |
| FR | 2 711 304 | 4/1995 |
| GB | 2 245 131 | 1/1992 |
| JP | 02207758 A * | 8/1990 |
| JP | 06032741 A * | 2/1994 |
| JP | 6-269250 | 9/1994 |
| JP | 10-229830 | 9/1998 |
| JP | 2002-360186 | 12/2002 |
| JP | 2002-370993 | 12/2002 |
| JP | 2003-210116 | 7/2003 |
| JP | 2003-299445 | 10/2003 |
| JP | 2004 254712 | 9/2004 |
| JP | 2005-218423 | 8/2005 |
| JP | 2005-278593 | 10/2005 |
| WO | WO 85/05015 | 11/1985 |
| WO | 00/59316 | 10/2000 |
| WO | 02/100188 | 12/2002 |
| WO | 2004/091307 | 10/2004 |
| WO | 2005/023019 | 3/2005 |

OTHER PUBLICATIONS

Chemnet.com; online, URL< http://www.chemnet.com/dict/dict—8016-65-7—en.html> one page, accessed Jul. 1, 2011.*
Sultan et al. Nutritional Profile of Indigenous Cultivar of Black Cumin Seeds and Antioxidant Potential of Its Fixed and Essential Oil; Pak. J. bot., 41(3): pp. 1321-1330 (2009).*
International Search Report issued in PCT/EP2007/050393; Apr. 23, 2007, 3 pages.
T. P. Heil et al., "Sensory Properties of Thiophenols and Alkylphenols Causing Flavor Tainting in Fish From the Upper Wisconsin River USA", J. of Environmental Science and Health Part B Pesticides Food Contaminants and Agricultural Wastes, vol. 24, No. 4, 1989, pp. 361-388.
Intrnational Standard ISO 3526, "Oil of sage, Spanish", Reference No. ISO 3526.2005(E), Third edition. Jul. 1, 2005, 9 pages.
International Standard ISO 9909, Oil of Dalmatian sage, (*Salvia officinalis* L.), Reference No. ISO 9909.1997(E), First edition, May 1, 1997, 7 pages.
Dea Baričevič et al., "Part 5, Pharmacology: The biological/pharmacological activity of the Origanum Genus," Taylor & Francis, pp. 177-213 (2002).
C. Brauge et al., "Effect of dietary carbohydrate levels n growth, body composition and glycaemia in rainbow trout, *Oncorhynchus mykiss*, reared in seawater," Aquaculture 123, Abstract only (1994).
M.J. Barbosa et al., "Effect of carotenoid source and dietary lipid content on blood astaxanthin concentration in rainbow trout (*Oncorhynchus mykiss*)," Aquaculture 176, pp. 331-341 (1999).
Japanese Office Action mailed Aug. 2, 2011 in corresponding Japanese Patent Application No. 2008-552767.
Japanese Office Action mailed Sep. 11, 2012 in corresponding Japanese Patent Application No. 2008-552767.

* cited by examiner

*Primary Examiner* — Patricia Leith
(74) *Attorney, Agent, or Firm* — Pillsbury Winthrop Shaw Pittman LLP

(57) ABSTRACT

A fish feed comprises carvacrol and/or *salvia* extract (provided that where the fish feed comprises carvacrol and not *salvia* extract the lipid content of the fish feed is at least 15 wt %). The *salvia* extract may be selected from extract of *Salvia officinalis* and extract of *Salvia lavandulifolia*. The carvacrol may be synthetic or may be extracted from *Origanum vulgare*.

19 Claims, No Drawings

FEED FOR FISH

CROSS REFERENCE TO RELATED APPLICATIONS

This is the U.S. National Phase of PCT/EP2007/050393, filed Jan. 16, 2007, which in turn claims priority to British application No. 0602426.9, filed Feb. 7, 2006, the entire contents of both of which are incorporated herein by reference.

The present invention relates to a feed for fish, to a method of making the feed, to a method of feeding fish with the feed and to fish fed with the feed.

Fish is an important source of protein for the world's population. It is recognised that consumption of fish per capita should be increased because of its positive health effects.

However, it is no longer possible to increase the quantity of fish caught in the wild, because of the effect on fish stocks. Some stocks of wild fish have collapsed already, and for other stocks the catch must be reduced for the stocks to be sustainable.

Aquaculture (fish farming) is therefore of increasing importance in supplying fish to the world's population.

Fish need protein, fat, minerals and vitamins in order to grow and to be in good health. The diet of carnivorous fish is particularly important.

Originally in the farming of carnivorous fish, whole fish or ground fish were used to meet the nutritional requirements of the farmed fish. Ground fish mixed with dry raw materials of various kinds, such as fish meal and starch, was termed soft or semi-moist feed. As farming became industrialized, soft or semi-moist feed was replaced by pressed dry feed. This was itself gradually replaced by extruded dry feed.

Today, extruded feed is nearly universal in the farming of a number of fish species such as various types of salmonid, cod, sea bass and sea bream.

The dominant protein source in dry feed for fish has been fish meal of different qualities. Fish meal and fish oil are obtained from so-called "industrial fish". The catch of industrial fish cannot be increased for the reasons set out above.

Industrial fish may for example be of North-European origin or of South-American origin, in particular fish caught off the coasts of Peru and Chile. The output of these countries fluctuates somewhat from one year to the next. At about 7 year intervals the weather phenomenon El Niño occurs, and severely reduces the output of industrial fish. This affects the availability of fish meal and fish oil on the world market, and prices rise considerably for these raw materials.

The aquaculture industry and especially the fish feed industry have predicted for several years that there will be a shortage of both fish meal and fish oil in the future. Other animal protein sources are also used for dry fish feed. Thus, it is known to use blood meal, bone meal, feather meal and other types of meal produced from other slaughterhouse waste, for example chicken meal. These are typically cheaper than fish meal and fish oil. However, in some geographic regions, such as Europe, there has been a prohibition against using such raw materials in the production of feeds for food-producing animals and fish.

It is also known to use vegetable protein such as wheat gluten, maize (corn) gluten, soya protein, lupin meal, pea meal, bean meal, rape meal, sunflower meal and rice flour. Soya is a low price raw material with high protein content and is available in very large quantities on a world-wide basis. Therefore, soya has been used in fish feeds for many years.

There is thus pressure to minimise the quantity of raw material used in fish feed for aquaculture.

In addition, aquaculture is capital intensive. There are investments in cages, pens or ponds, feeding automata, storage facilities and other infrastructure. The fish themselves have associated costs as they are purchased as fingerlings (e.g. trout and salmon species, sea bass, sea bream, turbot, halibut, cod) or wild caught (e.g. yellow tail, cod, saithe, tuna species).

The most important single cost in aquaculture is the cost of the feed. Labour costs are also important.

The selling price of the fish and the number of fish that are harvested determine the profitability of the operation.

A faster turnover has several positive results. First, it helps cash flow. Second, it improves risk management. Fish diseases are common, and the likelihood of an outbreak is higher over a long growing period. There is also a risk that fish will escape due to accidents, e.g. when shifting nets, or due to bad weather causing wrecked fish pens.

Turnover rate is determined by how fast the fish grow to a harvestable size. As an example, it takes from 12 to 18 months to raise Atlantic salmon from smolt (the physiological stage when the Atlantic salmon can first be transferred from fresh water to sea water) to harvestable size. Harvestable size is dependent on the fish species and market. Some markets for Atlantic salmon prefer fish larger than 6 kg. Rainbow trout is in some markets sold as portion sized and the weight is 300 g.

Growth rate is expressed as percentage increase in body mass from day to day (Specific Growth Rate, SGR). This is calculated as:

$$SGR = \left(\left(\frac{FinalW}{InitW}\right)^{1/Days} - 1\right) \cdot 100$$

FinalW=final weight
InitW=initial weight
Days=time from measuring initial weight to final weight The SGR does not take into account the amount of feed fed to obtain growth. It is a measure of growth rate only. A high SGR is dependent on the digestibility of the raw materials and how optimal the feed composition is with respect to protein and fat ratio, amino acid composition and composition of fatty acids. Microingredients such as vitamins and minerals must also be present in sufficient quantities.

Another important economic factor is how efficiently the fish grow on the feed. Fish growth is in practical terms protein deposition in the muscle (growth of muscle mass).

The common term to describe this is Feed Conversion Ratio (FCR) defined as:

FCR=Amount of feed fed (kg)/Net growth of the fish (kg)

FCR varies between fish species and also with the size of the fish. In Atlantic salmon FCR may typically be from 0.7 to 2. Industrial fish feed in the form of pressed feed and extruded feed contains low amounts of water, typically from 5 to 10%. The fish body has a much higher water content. This explains why the FCR may be lower than 1. An accurate comparison of the FCR of different feeds should take into account the water content of the feeds as water does not contribute to growth. Most precisely the FCR should be calculated on a dry matter basis. However, as the water content is within a narrow range, and it is cumbersome for the fish farmer to calculate dry matter FCR, FCR is normally calculated on the feed including water content.

There is also a distinction between the "biological FCR" and the "economic FCR". The biological FCR is on the individual fish level. It takes account of the actual feed eaten by the individual fish and its weight gain over the observed period. This is the true performance of the feed. As with SGR, biological FCR is a function of the digestibility of the nutrients, the balance between protein and energy (e.g. fat), the balance between the different amino acids and the presence of sufficient microingredients (such as vitamins and minerals).

In a commercial operation, however, there are numerous individual fish in each pen or pond (e.g. 10000 to 30000 individuals in each pen). Feeding cannot be observed on the individual level. The fish farmer is therefore more concerned about the economic FCR. This is on a cage level and is defined as the amount of feed fed to the cage and the increase in the cage's fish biomass over the observation period.

The economic FCR is higher than the biological FCR for several reasons. First, some feed is lost because feed pellets break apart in the feeding system and the broken pieces are too small to be eaten or are so small that they are recognised as dust. Second, some feed pellets are not eaten by the fish but just sink through the water column. Third, some feed is lost because the fish are fed to satiation, while feeding continues. This is known as overfeeding. Fourth, underfeeding may occur, in which case the FCR increases because a higher proportion of the protein in the feed will be used for metabolic purposes as opposed to for muscle deposition. Fifth, fish may escape through holes in the net. The initial biomass is determined by counting the individuals and by determining the initial weight by weighing sub-samples of the population. Wrong numbers have an impact on the economic FCR.

Thus, it is desirable to produce a fish feed which leads to good (high) SGR and good (low) biological and/or economic FCR.

To achieve the above objects, additives that can increase the digestibility of fat and or protein are of value. This can be measured by the "Apparent Digestibility Coefficient", calculated as:

$$ADC(\%) = 100 - \left(100 \cdot \left(\frac{\text{Yttrium in diet}}{\text{Yttrium in faeces}} \cdot \frac{\text{Nutrient in faeces}}{\text{Nutrient in diet}}\right)\right)$$

Yttrium is added to the diet for the purpose of calculating ADC, but is otherwise not a necessary component of fish feed.

JP2-207758 discloses a low fat fish feed which comprises one or more of various plant essential oils or components extracted therefrom including carvacrol. The fish feed is taught to protect fish against infectious diseases.

The present inventors have surprisingly found that including in fish feed either separately or together certain additives which can be extracted from plants or synthesised chemically helps to achieve high SGR and low FCR, thus giving a high fish turnover for a low feed input.

The additives are carvacrol and *salvia* (sage) extract.

Without wishing to be bound by this theory, the inventors believe that growth of fish is promoted by the additives because digestibility of fat by the fish is improved. It is believed that the two additives have similar effects.

Accordingly, in a first aspect, the present invention provides a fish feed comprising carvacrol and/or *salvia* extract, provided that where the fish feed comprises carvacrol and not *salvia* extract the lipid content of the fish feed is at least 15 wt %.

The term "fish feed" as used herein includes compositions as described below. Typically, fish feed includes fish meal as a component. Suitably, fish feed is in the form of flakes or pellets, for example extruded pellets.

The term "extract" as used herein includes compositions obtained by solvent extraction (which are also known as "extracted oils"), steam distillation (which are also known as "essential oils") or other methods known to the skilled person. Suitable extraction solvents include alcohols such as ethanol.

Preferably, the *salvia* extract is a concentrate. The term "*salvia*" as used herein includes plants of the *Salvia* genus of the Lamiaceae family. Preferred species of *salvia* are Dalmatian sage (*Salvia officinalis*) for example *Salvia officinalis* L. (essential oil described in ISO 9909:1997 (E)), and Spanish sage (*Salvia lavandulifolia*) for example *Salvia lavandulifolia* Vahl (essential oil described in ISO 3526:2005(E)).

*Salvia* extract is known to contain at least 4 active compounds. A typical chromatographic profile for *Salvia officinalis* L. shows α-pinene, camphene, limonene, 1,8-cineole, α-thujone, β-thujone, camphor, linalol and linalyl acetate, bornyl acetate and α-humulene. A typical chromatographic profile for *Salvia lavandulifolia* Vahl shows α-pinene, sabinene, limonene, 1,8-cineole, linalool, camphor, borneol, terpinen-4-ol, linalyl acetate, α-terpinyl acetate and sabinyl acetate.

*Salvia* extracts are commercially available.

The term "carvacrol" as used herein refers to 2-methyl-5 (1-methylethyl)-phenol (CAS 499-75-2). This compound can be obtained from oregano (*Origanum vulgare*) and other plants. A nature identical compound can be synthesised and is commercially available.

As digestibility of lipid is believed to be improved by the invention, it is desirable to have a high lipid content in the feed so that fish growth is promoted as much as possible. Certain fish (including salmonids) require high lipid feed to remain healthy. Preferably, the fish feed contains at least 15 wt % lipid, more preferably at least 20 wt % lipid, still more preferably at least 25 wt % lipid, for example, 25 to 35 wt % lipid.

The fish feed preferably comprises carvacrol in an amount of 0.005-0.5 wt % and/or *salvia* extract in an amount of at least 0.005-0.5 wt %. More preferably, the fish feed comprises carvacrol in an amount of 0.01-0.25 wt % and/or *salvia* extract in an amount of 0.01-0.25 wt %. Suitably, the fish feed comprises carvacrol in an amount of 0.01-0.05 wt %, for example 0.02-0.04 wt %, and/or *salvia* extract in an amount of about 0.01-0.05 wt %, for example 0.02-0.04 wt %.

Preferably, the fish feed has a proximate composition of 30-50 wt % protein, 3-15 wt % moisture and lipid as described above.

Preferably, the fish feed comprises one or more of:
sources of protein, carbohydrate and lipid (for example, fish meal, fish oil, animal meal (for example blood meal, feather meal, poultry meal, chicken meal and/or other types of meal produced from other slaughterhouse waste), animal fat (for example poultry oil), vegetable meal (e.g. soya meal, lupin meal, pea meal, bean meal, rape meal and/or sunflower meal), vegetable oil (e.g. rapeseed oil, soya oil), gluten (e.g. wheat gluten or corn gluten) and added amino acids (e.g. lysine));
vitamin premix;
mineral premix; and
pigment (e.g. canthaxanthin, astaxanthin).

In a second aspect, the invention relates to a method of making a fish feed as described above.

Preferably, the method comprises the steps of:
mixing ingredients in a mixer;
extrusion or pressing of pellets; and
coating the pellets with oil.

The carvacrol and/or *salvia* extract is suitably either added to the mixer or included in the coating oil.

Suitably, carvacrol is provided in the form of a mixture of carvacrol with a dry carrier such as silica (for example a 50:50 mixture by weight), or in the form of pure carvacrol.

Similarly, *salvia* extract is suitably provided in the form of a mixture of *salvia* extract with a dry carrier such as silica (for example a 50:50 mixture by weight), or in the form of pure *salvia* extract.

In a third aspect, the invention relates to use of a fish feed as described above for feeding fish. The feed is particularly suitable for feeding salmonids, including Atlantic salmon (*Salmo salar*), other salmon species and trout, and non-salmonids such as cod, sea bass, sea bream and eel. However, it can be fed to all types of fish, for example turbot, halibut, yellow tail, saithe, and tuna.

In a fourth aspect, the invention relates to a fish fed with a fish feed as described above.

In a fifth aspect, the invention relates to use of carvacrol and/or *salvia* extract for promoting growth of fish.

In a sixth aspect, the invention relates to use of carvacrol and/or *salvia* extract for improving lipid digestibility in fish.

Features described in relation to any aspect of the invention may be used in any other aspect of the invention.

The invention will be further described with reference to the non-limiting Examples.

General Method for Preparation of Pressed Fish Feed

The main raw materials are ground and mixed.

Microingredients are added to the mixer. The homogenous mix is conditioned by adding water and steam to the mass in a preconditioner. This starts a cooking process in the starch fraction (the binding component). The mass is fed into a pellet mill. The mass is forced through the mill's die and the strings are broken into pellets on the outside of the die. The moisture content is low and drying of the feed is not necessary. Additional oil may be sprayed onto the surface of pellets, but as the pellets are rather compact, the total lipid content rarely exceeds 24%. The added oil may be fish oil or vegetable oils, for example rape seed oil or soy oil, or a mixture of vegetable oils or a mixture of fish oil and vegetable oils. After oil coating, the pellets are cooled in a cooler and bagged.

General Method for Preparation of Extruded Fish Feed

The main raw materials are ground and mixed. Micro ingredients are added to the mixer. The homogenous mix is conditioned by adding water and steam to the mass in a preconditioner. Additional oil may also be added to the mass at this stage. This starts a cooking process in the starch fraction (the binding component). The mass is fed into an extruder. The extruder may be of the single screw or the twin-screw type. Due to the rotational movement of the mass in the extruder, the mass is further mixed. Additional oil, water and steam may be added to the mass in the extruder. At the end of the extruder, the mass has a temperature above 100° C. and a pressure above ambient pressure. The mass is forced through the openings in the extruder's die plate. Due to the relief in temperature and pressure, some of the moisture will evaporate immediately (flash off) and the extruded mass becomes porous. The strings are cut into pellets by a rotating knife. The water content is rather high (18-28%) and the pellets are therefore immediately dried to approximately 10% water content in a dryer. After the dryer, more oil may be added to the feed by spraying oil onto the surface of the feed, or by dipping the feed in oil. It is advantageous to add the oil to the feed in a closed vessel where the air pressure is below ambient (vacuum coating) so that the porous feed pellets absorb more oil. Feed containing more than 40% lipid may be produced this way. After the coater, the feed is cooled and bagged. Oil may be added at several places in the process as explained above, and may be fish oil or vegetable oils, by example rape seed oil or soy oil, or a mixture of vegetable oils or a mixture of fish oil and vegetable oils.

EXAMPLE 1

The feeds used in Example 1 had a proximate composition of protein (45.6-47.4 wt %), lipid (30.2-32.2 wt %), moisture (5.2-6.2 wt %) and ash (5.4-5.8 wt %).

A control feed was prepared from fish meal (407.4 g), soybean meal (55.8 g), corn gluten (196.1 g), wheat (88.0 g), fish oil (247.3 g), mineral and vitamin premixes (3.8 g), yttrium premix (1.0 g, used to measure lipid digestibility as discussed below) and astaxanthin preparation (0.6 g). Pellets were extruded using the process explained above and coated with the fish oil.

Test feeds containing 0.1 wt % and 0.2 wt % carvacrol formulation (containing 50 wt % carvacrol and 50 wt % silica carrier) were prepared. The amount of active substance was 500 and 1000 mg per kg feed, respectively. In the comparison feeds, the amount of wheat was reduced to 87.0 g and 86.0 g respectively. The carvacrol formulation was added with the other microingredients to the mixer before preconditioning.

Pellet size was 4 mm.

Test feeds containing 0.1 wt % and 0.2 wt % formulation of *Salvia officinalis* salvia extract (containing 50 wt % *salvia* extract and 50 wt % silica carrier) were prepared in a similar way.

The feed was fed to Atlantic salmon (*Salmo salar*) weighing 169 g (+3 g) at the onset of the study. The fish was stocked in tanks (1 m×1 m). There were 30 fish in each tank. Sea water temperature was 11.8° C. (±0.5° C.). The fish were fed for 67 days. The study was run in triplicate.

The results are shown in Table 1.

TABLE 1

| Feed | Initial weight (g) | Final weight (g) | Specific growth rate | Feed conversion ratio |
| --- | --- | --- | --- | --- |
| Control | 170 ± 2.77 | 330 ± 13 | 0.99 ± 0.08 | 0.91 ± 0.05 |
| Carvacrol 0.05 wt % | 169 ± 3.54 | 339 ± 18 | 1.04 ± 0.05 | 0.91 ± 0.05 |
| Carvacrol 0.1 wt % | 171 ± 0.63 | 354 ± 6 | 1.09 ± 0.03 | 0.87 ± 0.03 |
| *Salvia* 0.05 wt % | 170 ± 2.89 | 339 ± 5 | 1.03 ± 0.03 | 0.88 ± 0.03 |
| *Salvia* 0.1 wt % | 171 ± 1.18 | 354 ± 11 | 1.09 ± 0.04 | 0.83 ± 0.04 |

It can be seen that increasing amounts of carvacrol and increasing amounts of *salvia* extract each lead to increased fish growth and improved feed utilisation.

EXAMPLE 2

The feeds used in Example 2 had a proximate composition of protein (46.0-46.9 wt %), lipid (30.8-31.9 wt %), moisture (4.9-5.6 wt %) and ash (7.4-7.7 wt %).

Control and comparison feeds were prepared as in Example 1. *Salvia lavandulifolia* salvia extract (CAS 8016-65-7) was used.

Pellet size was 4 mm.

The feed was fed to Atlantic salmon (*Salmo salar*) weighing 199 g (±2.4 g) at the onset of the study. The fish were stocked in tanks (1 m×1 m). There were 35 fish in each tank. Sea water temperature was 12° C. The fish were fed for 82 days. The study was run in triplicate.

The results are shown in Table 2 (SE stands for "standard error").

TABLE 2

| Feed | Initial weight (g) | SE | Final weight (g) | SE | Specific growth rate | SE | Feed conversion ratio | SE |
|---|---|---|---|---|---|---|---|---|
| Control | 198 | 0.95 | 488 | 5.50 | 1.10 | 0.08 | 0.74 | 0.03 |
| Carvacrol 0.05 wt % | 199 | 1.29 | 512 | 6.81 | 1.16 | 0.01 | 0.68 | 0.02 |
| Carvacrol 0.1 wt % | 200 | 1.19 | 503 | 6.89 | 1.13 | 0.01 | 0.70 | 0.01 |
| *Salvia* 0.05 wt % | 199 | 1.23 | 490 | 6.18 | 1.10 | 0.01 | 0.73 | 0.00 |
| *Salvia* 0.1 wt | 198 | 1.18 | 505 | 6.57 | 1.15 | 0.02 | 0.70 | 0.02 |

It can be seen that increasing amounts of carvacrol and increasing amounts of *salvia* extract each lead to increased fish growth and improved feed utilisation.

Lipid digestibility was determined using a standard method and the results are shown in Table 3.

TABLE 3

| Feed | ADC (%) lipid (%) | SE |
|---|---|---|
| Control | 96.39 | 0.35 |
| Carvacrol 0.05 wt % | 95.78 | 0.07 |
| Carvacrol 0.1 wt % | 97.65 | 0.02 |
| *Salvia* 0.05 wt % | 98.19 | 0.16 |
| *Salvia* 0.1 wt % | 98.20 | 0.19 |

It can be seen that increasing amounts of carvacrol and increasing amounts of *salvia* extract each lead to increased lipid digestibility. Lipid digestibility for the groups fed *salvia* extract at the 0.05 wt % as well as the 0.1 wt % level were significantly higher than for the control group.

EXAMPLE 3

The feeds used in Example 3 had a proximate composition of protein (44.3-46.2 wt %), lipid (28.2-31.4 wt %) and moisture (6.0-6.5 wt %).

Control feed was prepared from South-American fish meal (526.2 g), soybean meal (40.0 g), corn gluten (79.0 g), wheat (120.4 g), South-American fish oil (230.3 g), mineral and vitamin premixes (2.5 g), yttrium premix (1.0 g), and astaxanthin preparation (0.6 g). Pellets were extruded using the process explained above and coated with the fish oil.

Test feeds were prepared containing carvacrol and/or *salvia* extract (*Salvia lavandulifolia*). Carvacrol and/or *salvia* extract were each added as 100% oil. Two different inclusion levels of separate carvacrol and *salvia* extract (0.5 g/kg and 1.0 g/kg) were tested.

Two test feeds were prepared with a combination of carvacrol and *salvia* extract. The inclusion levels were 1.0 g carvacrol and 0.2 g/kg *salvia* extract, and 0.5 g/kg carvacrol and 0.5 g/kg *salvia* extract, respectively. The carvacrol oil and/or *salvia* extract was mixed with the fish oil and coated onto the surface of the pellets by vacuum coating after drying of the pellets.

Pellet size was 3 mm for all feeds.

The feed was fed to Atlantic salmon (*Salmo salar*) weighing 156 g (+13 g) at the onset of the study. The fish was stocked in tanks holding 100 L water. There were 25 fish in each tank. Sea water temperature was 8.9° C.±0.2° C. The fish were fed for 96 days. The study was run with four control groups and one tank each for the different inclusion levels of carvacrol, *salvia* extract or combined carvacrol and *salvia*.

Apparent digestibility was determined for protein, the saturated fatty acid C16:0, the sum of all saturated fatty acids and the total lipid. The results are shown in Table 4.

TABLE 4

| Feed | ADC protein (%) (g) | ADC C16:0 (%) (g) | ADC saturated fatty acids (%) | ADC total lipid (%) |
|---|---|---|---|---|
| Control | 86.8 | 69.2 | 69.8 | 87.8 |
| Carvacrol 0.05 wt % | 88.8 | 75.3 | 75.5 | 89.2 |
| Carvacrol 0.10 wt % | 87.6 | 74.0 | 74.4 | 89.2 |
| *Salvia* 0.05% | 87.7 | 73.0 | 73.1 | 89.1 |
| *Salvia* 0.10 wt % | 88.8 | 76.9 | 77.0 | 90.6 |
| Carvacrol 0.10 wt %/ *Salvia* 0.02 wt % | 86.8 | 75.1 | 75.3 | 89.9 |
| Carvacrol 0.05 wt %/ *Salvia* 0.05 wt % | 87.8 | 75.3 | 75.6 | 89.4 |

It can be seen that increasing amounts of carvacrol and increasing amounts of *salvia* extract each lead to increased lipid digestibility and protein digestibility.

It will be appreciated that, although the invention has been described with reference to examples, various modifications are possible within the scope of the invention.

The invention claimed is:

1. A method of promoting growth of fish, improving lipid digestibility or improving protein digestibility of feed in fish, comprising feeding fish with coated fish feed pellets coated with carvacrol and *Salvia* essential oil, wherein said coated fish feed pellets comprise at least 15% by weight of lipids, 0.005-0.5 wt % of carvacrol and 0.005-0.5 wt % of a *Salvia* essential oil, and wherein said *Salvia* essential oil is selected from a) *Salvia officinalis* L. essential oil comprising α-thujone, β-thujone, camphor, linalool, linalyl acetate, bornyl acetate and α-humulene or b) *Salvia lavendulifolia* essential oil comprising α-pinene, sabinene, limonene, 1,8-cineole, linalool, camphor, borneol, linalyl acetate, α-terpinyl acetate and sabinyl acetate.

2. A method as claimed in claim 1, wherein the carvacrol is synthetic or is extracted from *Origanum vulgare*.

3. A method as claimed in claim 1, wherein the fed fish are salmonids.

4. A method as claimed in claim 1, wherein the fed fish are Atlantic salmon.

5. A method as claimed in claim 1, wherein the *Salvia* essential oil is *Salvia lavandulifolia* extract CAS 8016-65-7.

6. A method as claimed in claim 1, wherein the coated fish feed pellets comprise sources of protein and carbohydrate.

7. A method as claimed in claim 1, wherein the coated fish feed pellets has have a lipid content of at least 20 wt %.

8. A method as claimed in claim 7, wherein the coated fish feed pellets has have a lipid content of at least 25 wt %.

9. A method as claimed in claim 1, wherein the coated fish feed pellets are extruded or pressed pellets.

10. A method as claimed in claim 1, wherein the coated fish feed pellets comprise 25-35 wt % of lipids.

11. A method as claimed in claim 10, wherein the coated fish feed pellets include fish meal as a component.

12. A method as claimed in claim 1, wherein the coated fish feed pellets include fish meal as a component.

13. A coated fish feed pellet coated with carvacrol and *Salvia* essential oil, wherein said coated fish feed pellet comprises at least 15% by weight of lipids, 0.005-0.5 wt % of carvacrol and 0.005-0.5 wt % of a *Salvia* essential oil, and wherein said *Salvia* essential oil is selected from a) *Salvia officinalis* L. essential oil comprising α-thujone, β-thujone, camphor, linalool, linalyl acetate, bornyl acetate and α-humulene or b) *Salvia lavendulifolia* essential oil comprising α-pinene, sabinene, limonene, 1,8-cineole, linalool, camphor, borneol, terpine-4-ol, linalyl acetate, α-terpinyl acetate and sabinyl acetate.

14. The coated fish feed pellet as claimed in claim 13, wherein the carvacrol is synthetic or is extracted from *Origanum vulgare*.

15. The coated fish feed pellet as claimed in claim 13, wherein the *Salvia* essential oil is *Salvia* lavandulifolia extract CAS 8016-65-7.

16. The coated fish feed pellet as claimed in claim 13, wherein the coated fish feed pellet comprises sources of protein and carbohydrate.

17. The coated fish feed pellet as claimed in claim 13, comprising a lipid content of at least 20 wt %.

18. The coated fish feed pellet as claimed in claim 13, comprising a lipid content of at least 25 wt %.

19. The coated fish feed pellet as claimed in claim 13, wherein the coated fish feed pellet is an extruded or pressed pellet.

* * * * *

UNITED STATES PATENT AND TRADEMARK OFFICE
CERTIFICATE OF CORRECTION

PATENT NO. : 8,951,584 B2
APPLICATION NO. : 12/278536
DATED : February 10, 2015
INVENTOR(S) : Wolfgang Koppe et al.

It is certified that error appears in the above-identified patent and that said Letters Patent is hereby corrected as shown below:

On title page, Item (56) References Cited - Foreign Patent Documents
      after "JP 02207758 A * 8/1990"
      insert --JP 92-75745 8/1990--.

On title page, Item (56) References Cited - Other Publications, Line 21
      replace "levels n growth, body"
      with --levels on growth, body--.

Signed and Sealed this
Twelfth Day of May, 2015

Michelle K. Lee
*Director of the United States Patent and Trademark Office*